(12) United States Patent
Kloster et al.

(10) Patent No.: US 11,967,419 B2
(45) Date of Patent: Apr. 23, 2024

(54) INFORMED PATIENT CONSENT THROUGH VIDEO TRACKING

(71) Applicant: inFormed Consent LLC, Eden Prairie, MN (US)

(72) Inventors: Daniel R. Kloster, Fairway, KS (US); Jason Blake Penrod, Overland Park, KS (US)

(73) Assignee: inFormed Consent LLC, Eden Prairie, MN (US)

( * ) Notice: Subject to any disclaimer, the term of this patent is extended or adjusted under 35 U.S.C. 154(b) by 0 days.

(21) Appl. No.: 17/983,132

(22) Filed: Nov. 8, 2022

(65) Prior Publication Data

US 2023/0223139 A1    Jul. 13, 2023

Related U.S. Application Data

(63) Continuation of application No. 17/573,367, filed on Jan. 11, 2022, now Pat. No. 11,501,875.

(51) Int. Cl.
| | |
|---|---|
| *G06V 40/18* | (2022.01) |
| *G06V 40/16* | (2022.01) |
| *G16H 15/00* | (2018.01) |
| *G16H 40/20* | (2018.01) |
| *H04N 5/76* | (2006.01) |

(52) U.S. Cl.
CPC .......... *G16H 40/20* (2018.01); *G06V 40/166* (2022.01); *G06V 40/174* (2022.01); *H04N 5/76* (2013.01)

(58) Field of Classification Search
USPC ............... 705/3, 50, 80, 1.1, 400, 500, 901
See application file for complete search history.

(56) References Cited

U.S. PATENT DOCUMENTS

| | | | | |
|---|---|---|---|---|
| 2010/0094650 | A1* | 4/2010 | Tran | G16H 40/20 705/2 |
| 2011/0106557 | A1* | 5/2011 | Gazula | G06Q 10/10 715/740 |
| 2017/0032092 | A1* | 2/2017 | Mink | G06Q 10/1095 |
| 2018/0042544 | A1* | 2/2018 | Graham | A61B 5/6898 |

OTHER PUBLICATIONS

Matthew Field, Oxford graduates in line for $100m payday after sale of start-up they founded at university, The Telegraph, Feb. 7, 2024, https://web.archive.org/web/20240207173446/https://www.telegraph.co.uk/business/2024/02/07/oxford-graduates-onfido-start-up-sale-100m/.

Chris Hooper, How To Fight Fraud: Leveraging Video for Powerful Assistance, Veriff, Nov. 24, 2020, https://www.veriff.com/fraud/learn/how-video-helps-fight-fraud.

* cited by examiner

*Primary Examiner* — Daquan Zhao
(74) *Attorney, Agent, or Firm* — Erise IP, P.A.

(57) ABSTRACT

A system, method, and computer-readable media for obtaining the informed consent of a patient for a medical procedure. Specifically, a video describing a medical procedure may be provided to the patient through a client device having two display portions. As the video is playing in a first portion, the client device may capture the patient watching the video and display the captured image on the second portion. The entire display of the client device may be recorded, providing a record that the patient has watched the video describing the medical procedure and consents to the medical procedure.

20 Claims, 7 Drawing Sheets

INFORMED PATIENT CONSENT THROUGH VIDEO TRACKING

RELATED APPLICATIONS

This application is a continuation, and claims priority benefit, with regard to all common subject matter, of earlier-filed U.S. patent application Ser. No. 17/573,367, filed Jan. 11, 2022, and entitled "INFORMED PATIENT CONSENT THROUGH VIDEO TRACKING," now U.S. Pat. No. 11,501,875, issued on Nov. 15, 2022, ("the '875 patent"). The identified earlier-filed patent is hereby incorporated by reference in their entirety into the present application

TECHNICAL FIELD

Embodiments of the invention relate to obtaining the informed consent of a person for a procedure or process. More specifically, embodiments of the invention relate to methods, systems, and computer readable media of obtaining patient informed consent of a medical procedure through the recording and tacking of a patient during a video demonstration.

Planned medical procedures and surgeries are oftentimes presented to patients as audio descriptions from a doctor or other medical provider prior to performance of the medical procedure. These audio descriptions can be delivered to patients just hours, or minutes, before the medical procedure. Surgery and other medical procedures, even relatively minor ones, can be high stress or intense experiences for patients. Accordingly, when descriptions of surgeries or medical procedure are presented to a patient, a patient is typically expected to retain only a fraction of the material and disclosure provided by the medical provider.

Traditional methods of presenting information to patients are rife with limitations and risks, for both patients and medical providers. Patients often have difficulty in remembering all the details of the described procedure, such as associated risks or follow-up treatment plans. Every medical procedure contains the possibility of complications and risk, and even in correctly performed procedures, negative results can occur. When negative results or complications occur, medical malpractice lawsuits are likely to follow. Even when patients are provided with descriptions of the medical procedures and associated risks, the lack of a recorded storage of the patient receiving the description leads to prolonged litigation with patients asserting that they were not informed of the risks associated with the procedure. Even if the medical provider informed the patient of the risks, the lack of a concrete record leads to a battle of credibility.

Accordingly, what is needed is a system and method of providing descriptions with medical procedures to patients and recording the process, providing a permanent and definite record of the patient's informed consent to the medical procedure, including associated risks.

SUMMARY

Embodiments of the invention solve the above-mentioned problems by providing a system, method, and computer-readable media for establishing a framework for managing application permissions in a group-based communication system.

A first embodiment of the invention is directed to one or more non-transitory computer-readable media storing computer-executable instructions that, when executed by a processor, perform a method of: providing, at a first portion of a display of a client device, a video of a medical procedure to a patient; simultaneously capturing a facial detection of the patient during the video of the medical procedure; displaying the facial detection of the patient in a second portion of the display of the client device, wherein the first portion and the second portion are simultaneously displayed on the display of the client device; recording the display of the client device, wherein the first portion and the second portion are recorded as a captured video recording; monitoring a position of the patient during an entire duration of the video of the medical procedure; and upon completion of the video of the medical procedure, obtaining an affirmative consent from the patient.

A second embodiment of the invention is directed to a method of: providing, at a first portion of a display of a client device, a video of a medical procedure to a patient, wherein the client device is in a patient mode; simultaneously capturing a facial detection of the patient during the video of the medical procedure; displaying the facial detection of the patient in a second portion of the display of the client device, wherein the first portion and the second portion are simultaneously displayed on the display of the client device; recording the display of the client device, wherein the first portion and the second portion are recorded as a captured video recording; and monitoring a position of the patient during an entire duration of the video of the medical procedure.

A third embodiment of the invention is directed to a system for obtaining medical consent of a patient, the system comprising: a data store; a processor; and one or more non-transitory computer-readable media storing computer-executable instructions that, when executed by the processor, perform a method for obtaining medical consent from a patient, the method comprising: responsive to a verification of the patient, providing, at a first portion of a display of a client device, a video of a medical procedure to a patient; simultaneously capturing a facial detection of the patient during the video of the medical procedure; displaying the facial detection of the patient in a second portion of the display of the client device, wherein the first portion and the second portion are simultaneously displayed on the display of the client device; recording the display of the client device, wherein the first portion and the second portion are recorded as a captured video recording; monitoring a position of the patient during an entire duration of the video of the medical procedure; and upon completion of the video of the medical procedure, obtaining an affirmative consent from the patient.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the invention will be apparent from the following detailed description of the embodiments and the accompanying drawing figures.

BRIEF DESCRIPTION OF THE DRAWING FIGURES

Embodiments of the invention are described in detail below with reference to the attached drawing figures, wherein.

Figure 1:
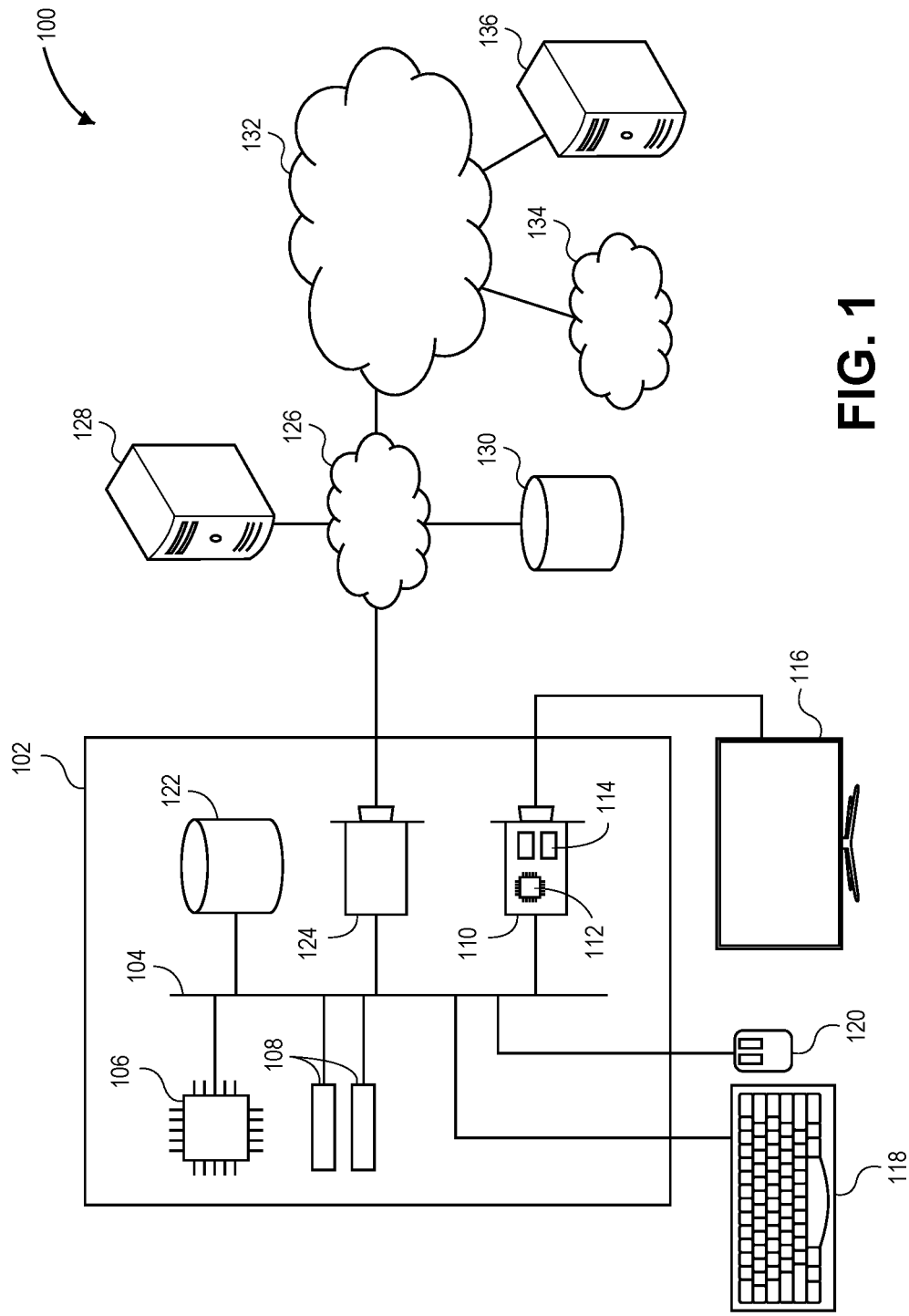
FIG. 1 depicts an exemplary hardware platform for certain embodiments of the invention.

The drawing figures do not limit the invention to the specific embodiments disclosed and described herein. The drawings are not necessarily to scale, emphasis instead being placed upon clearly illustrating the principles of the invention.

DETAILED DESCRIPTION

The following detailed description references the accompanying drawings that illustrate specific embodiments in which the invention can be practiced. The embodiments are intended to describe aspects of the invention in sufficient detail to enable those skilled in the art to practice the invention. Other embodiments can be utilized, and changes can be made without departing from the scope of the invention. The following detailed description is, therefore, not to be taken in a limiting sense. The scope of the invention is defined only by the appended claims, along with the full scope of equivalents to which such claims are entitled.

In this description, references to "one embodiment," "an embodiment," or "embodiments" mean that the feature or features being referred to are included in at least one embodiment of the technology. Separate references to "one embodiment," "an embodiment," or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments but is not necessarily included. Thus, the technology can include a variety of combinations and/or integrations of the embodiments described herein.

Broadly, embodiments of the present invention are directed to methods, systems, and computer-readable media of an informed consent software configured for presenting videos that outline the details of a medical procedure or surgery to a patient. Specifically, in some embodiments, a medical procedure video may be presented to a patient on the display window of a client device, such as a smartphone or tablet, having a front facing camera. As the patient is watching the medical procedure video, the front facing camera of the client device may capture video of the patient, and in real time, display the patient in a second display window of the client device. Thus, the display of the client device can comprise two display windows, a first display window playing the medical procedure video and a second display window showing the patient watching the medical procedure video. To preserve a record of the patient watching the medical procedure video, the entire display of the client device can be recorded, providing a single video file showing the patient watching the medical procedure video. Through such recording, a patient's informed consent to a medical procedure may be obtained with a permanent record verifying the patient's consent.

FIG. 1 illustrates an exemplary hardware platform for certain embodiments of the invention. Computer 102 can be a desktop computer, a laptop computer, a server computer, a mobile device such as a smartphone or tablet, or any other form factor of general- or special-purpose computing device. Depicted with computer 102 are several components, for illustrative purposes. In some embodiments, certain components may be arranged differently or absent. Additional components may also be present. Included in computer 102 is system bus 104, whereby other components of computer 102 can communicate with each other. In certain embodiments, there may be multiple busses, or components may communicate with each other directly. Connected to system bus 104 is central processing unit (CPU) 106. Also attached to system bus 104 are one or more random-access memory (RAM) modules 108. Also attached to system bus 104 is graphics card 110. In some embodiments, graphics card 110 may not be a physically separate card, but rather may be integrated into the motherboard or the CPU 106. In some embodiments, graphics card 110 has a separate graphics-processing unit (GPU) 112, which can be used for graphics processing or for general purpose computing (GPGPU). Also on graphics card 110 is GPU memory 114. Connected (directly or indirectly) to graphics card 110 is display 116 for user interaction. In some embodiments, no display is present, while in others it is integrated into computer 102. Similarly, peripherals such as keyboard 118 and mouse 120 are connected to system bus 104. Like display 116, these peripherals may be integrated into computer 102 or absent. In some embodiments, additional peripherals such as a microphone or video camera may also be present and connected to system bus 104. In some embodiments, such peripherals may be detachable connected to computer 102 via a wired or wireless connection. In other embodiments, such as a tablet or smartphone, these peripherals are integrated into computer 102. Also connected to system bus 104 is local storage 122, which may be any form of computer-readable media and may be internally installed in computer 102 or externally and removably attached.

Computer-readable media include both volatile and nonvolatile media, removable and nonremovable media, and contemplate media readable by a database. For example, computer-readable media include (but are not limited to) RAM, ROM, EEPROM, flash memory or other memory technology, CD-ROM, digital versatile discs (DVD), holographic media or other optical disc storage, magnetic cassettes, magnetic tape, magnetic disk storage, and other magnetic storage devices. These technologies can store data temporarily or permanently. However, unless explicitly specified otherwise, the term "computer-readable media" should not be construed to include physical, but transitory, forms of signal transmission such as radio broadcasts, electrical signals through a wire, or light pulses through a fiber-optic cable. Examples of stored information include computer-useable instructions, data structures, program modules, and other data representations.

Finally, network interface card (NIC) 124 is also attached to system bus 104 and allows computer 102 to communicate over a network such as network 126. NIC 124 can be any form of network interface known in the art, such as Ethernet, ATM, fiber, Bluetooth, or Wi-Fi (i.e., the IEEE 802.11 family of standards). NIC 124 connects computer 102 to local network 126, which may also include one or more other computers, such as computer 128, and network storage, such as data store 130. Generally, a data store such as data store 130 may be any repository from which information can be stored and retrieved as needed. Examples of data stores include relational or object-oriented databases, spreadsheets, file systems, flat files, directory services such as LDAP and Active Directory, or email storage systems. A data store may be accessible via a complex Application Programming Interface (API) (such as, for example, Structured Query Language), a simple API providing only read, write, and seek operations, or any level of complexity in between. Some data stores may additionally provide management functions for data sets stored therein such as backup or versioning. Data stores can be local to a single computer such as computer 128, accessible on a local network such as local network 126, or remotely accessible over Internet 132. Local network 126 is in turn connected to Internet 132, which connects many networks such as local network 126, remote network 134 or directly attached computers such as computer 136. In some embodiments, computer 102 can itself be directly connected to Internet 132.

Figure 2:
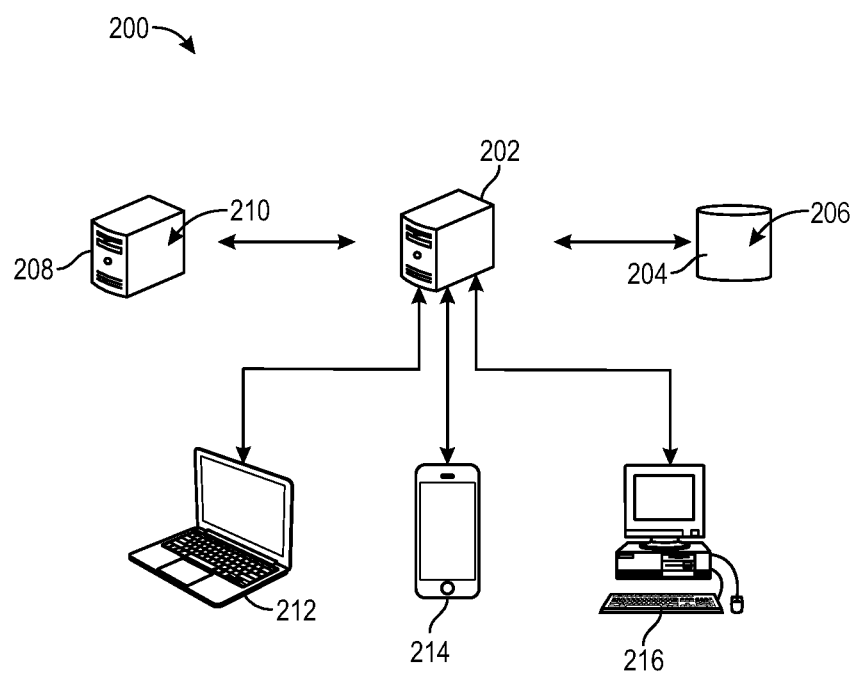
FIG. 2 depicts an exemplary diagram illustrating components of a system for carrying out embodiments of the invention.

Turning now to FIG. 2, an exemplary diagram illustrating components of a system for carrying out embodiments of the invention is depicted and referred to with reference numeral 200. System 200 may comprise a hospital server 202, which may act as a host for the informed consent software, data, and other implementations necessary to carry out the embodiments described herein. For example, hospital server 202 may be a dedicated server, a shared server, a virtual machine instance in a cloud computing environment, or any other form of computing device described above with respect to FIG. 1. Although a single hospital server 202 is depicted, embodiments of multiple server systems are also contemplated so as to provide scale, redundancy, and/or isolation between different instances of system 200. For example, a hospital may not wish to have its patient information stored on the same server as another hospital or on a server that is open or available to the public.

Further, as depicted in FIG. 2, in some embodiments, hospital server 202 may be communicatively coupled to a patient record store 204, which may be configured for storing patient information related to one or more patients and/or hospital information related to employees of the hospital. In some embodiments, patient record store 204 may be directly connected to hospital server 202; however, any form of communication connection (for example, network-attached storage (NAS), a network file system (NFS), or cloud-based storage) can be employed. Broadly speaking, patient record store 204 stores all of the durable patient information used by hospital server 202. For example, patient record store 204 may store the medical history of one or more patients, such as prescription information, surgery history, or other electronic medical record information. In some embodiments, patient record store 204 may further store patient profiles 206, associated with a particular patient for use with system 200. As described in greater detail below, patient profiles 206 may be online accounts associated with individual patients of users of the informed consent software. For example, the patient profiles 206 may comprise the name and other identifying information about the patient, the patient's contact information, the patient's scheduled appointments and procedures, the patient's consent status for specific procedures, among other patient information. In some embodiments, and as described in greater detail below, patient record store 204 may also be configured for storing recorded videos of the patient viewing a medical procedure video. Because of the sensitive nature of the patient data and other stored data, patient record store 204 may further be configured to encrypt the stored data or comprise pre-determined levels of security measures for protecting the patient data. Optionally or additionally, patient record store 204 may also be configured for storing user profiles, associated with the physicians, nurses, or other users of the informed consent software. As described in greater detail below, users of the informed consent software may be sorted into certain roles, with different roles having different authorizations or access to features or data of the informed consent software. Accordingly, the user profiles may be configured for storing the role of the associated user.

Hospital server 202 may further be communicatively coupled to medical procedure video server 208. In some embodiments, medical procedure video server 208 may host one or more medical procedure videos 210, which may be videos, audio descriptions, text-based descriptions, and/or other outlines or descriptions of medical procedures and/or surgeries. For example, a third-party company may create medical procedure videos 210 and upload or transmit the medical procedure videos 210 to medical procedure video server 208 for storage. Once uploaded, medical procedure video server 208 may transmit the medical procedure videos 210 to hospital server 202 upon a request or call. In some embodiments, medical procedure video server 208 may be in communication with a plurality of hospital servers 202, such that medical procedure videos 210 may be shared to multiple hospital server 202 for use by a plurality of hospitals. Similar to the connection methods described above, medical procedure video server 208 may be directly or indirectly connected to hospital server 202.

As used herein, "medical procedure videos" refers to pre-made live-action videos, animations, audio descriptions, or other forms of media that provide an explanation of a medical procedure or surgery. Specifically, the medical procedure videos may include a detailed video and audio description of a medical procedure or surgery, including a description of the pre-procedure, how the procedure will be performed, post-procedure care, any risks associated with the procedure, any potential complications that may occur, the benefits of the procedure, and/or any other information that may aid the patient in being informed about the procedure so that they can consent. The medical procedure videos may be created by an independent third-party from users of the informed consent software, such as a dedicated production company, that may upload the videos to the medical procedure video server 208 for use by hospitals, physicians, and other users of the informed consent software.

Hospital server 202 is further communicatively coupled to at least one client device, including for example, the depicted client devices 212, 214, and 216, respectively. As depicted in FIG. 2, client devices 212, 214, and 216 may be any form of computing device discussed above with respect to FIG. 1. In particular, and by way of non-limiting example, client device 212 may be a laptop computer, client device 214 may be a smartphone, and client device 216 may be a desktop computer. In some embodiments, client devices 212, 214, and/or 216 may be directly connected to hospital server 202 via a direct connection, such as an Ethernet cable. In some embodiments, client devices 212, 214, and/or 216 may be indirectly connected to hospital server 202 via an indirect connection, such a through a cellular network, wi-fi, or other indirect means. Embodiments of the present invention may be accessible via a web browser of the client device or a dedicated software such as an application.

In some embodiments, and as described in greater detail below, embodiments of the present invention may utilize one or more peripherals of the client devices for capturing and/or recording certain information, such as facial detection, for example. Non-limiting examples of peripherals of client devices that may be used include but are not limited to: cameras (including built in cameras and external webcams), microphones (including built in microphones and external microphones), keyboards (including touchscreen keyboards), mice, and other peripherals.

Exemplary embodiments, as described herein, refer to a hospital or other medical provider setting, with the medical procedure videos further described as outlining medical procedures or surgeries. However, it will be appreciated that the informed consent software may be applied in any scenario for recording a person watching or observing a video or a live demonstration, and is not intended to be limited to medical settings. Rather, exemplary embodiments of the present invention may be utilized in any scenario for recording a multiple window display, with a first window displaying a video, or captured recording of an event and a second window displaying a captured image of a person viewing the video or captured recording. For example, embodiments of the present invention may be used in a variety of training or teaching applications, to provide a record that a person has watched a training or explanatory video. In another example, the present invention may be used for monitoring a person working or interacting with on a client device and provide a record of what the person is viewing or interacting with on the client device. However, it will be appreciated that the present technology may be applied in any scenario for recording a first display showing a captured recording of a person watching a video, demonstration, screen, or event, while simultaneously displaying and recording the video, demonstration, screen, or event.

Figure 3A:
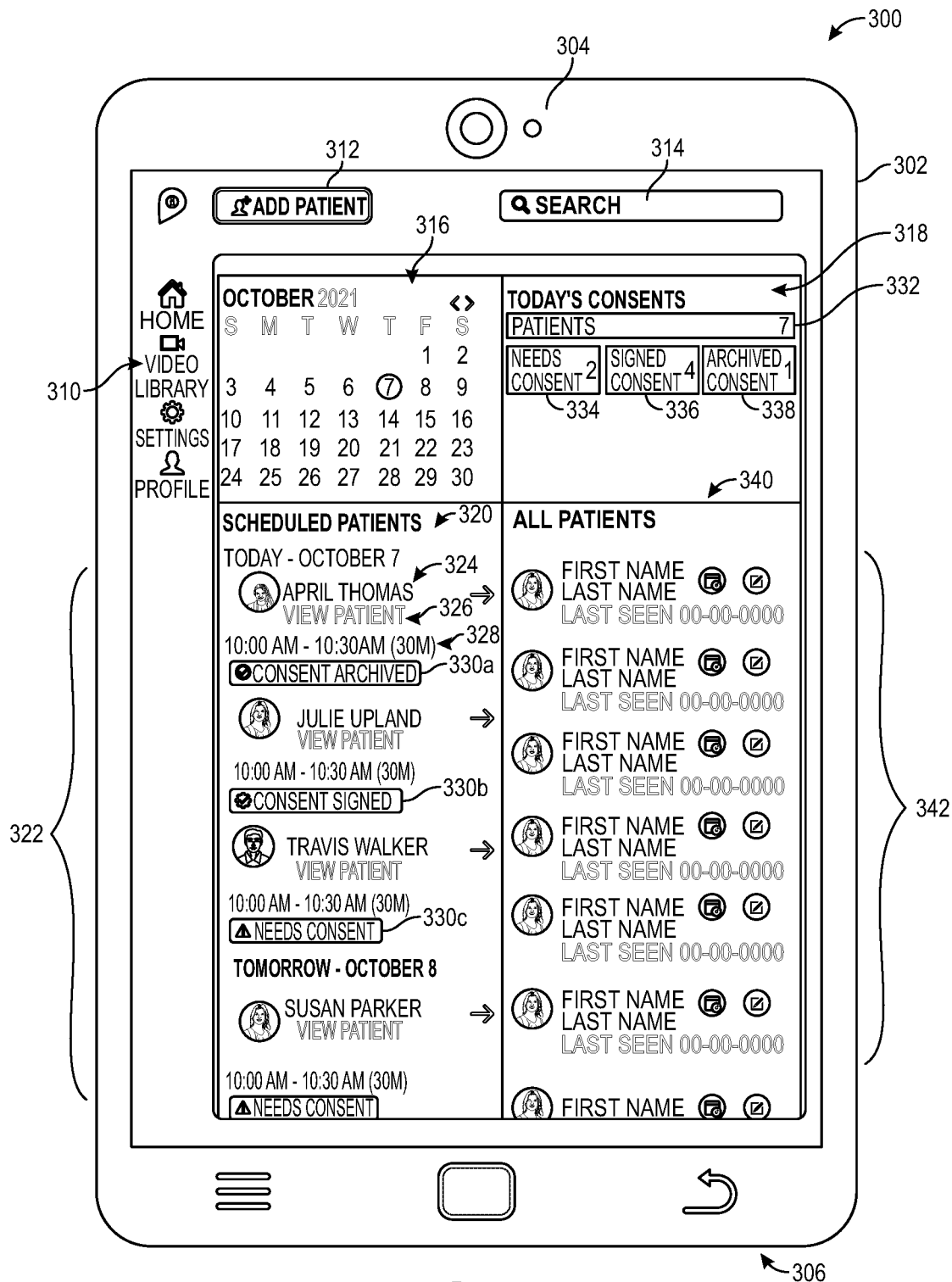
FIG. 3A illustrates a user interface of the run-time of an informed consent software in a provider mode in accordance with certain embodiments.
Figure 3B:
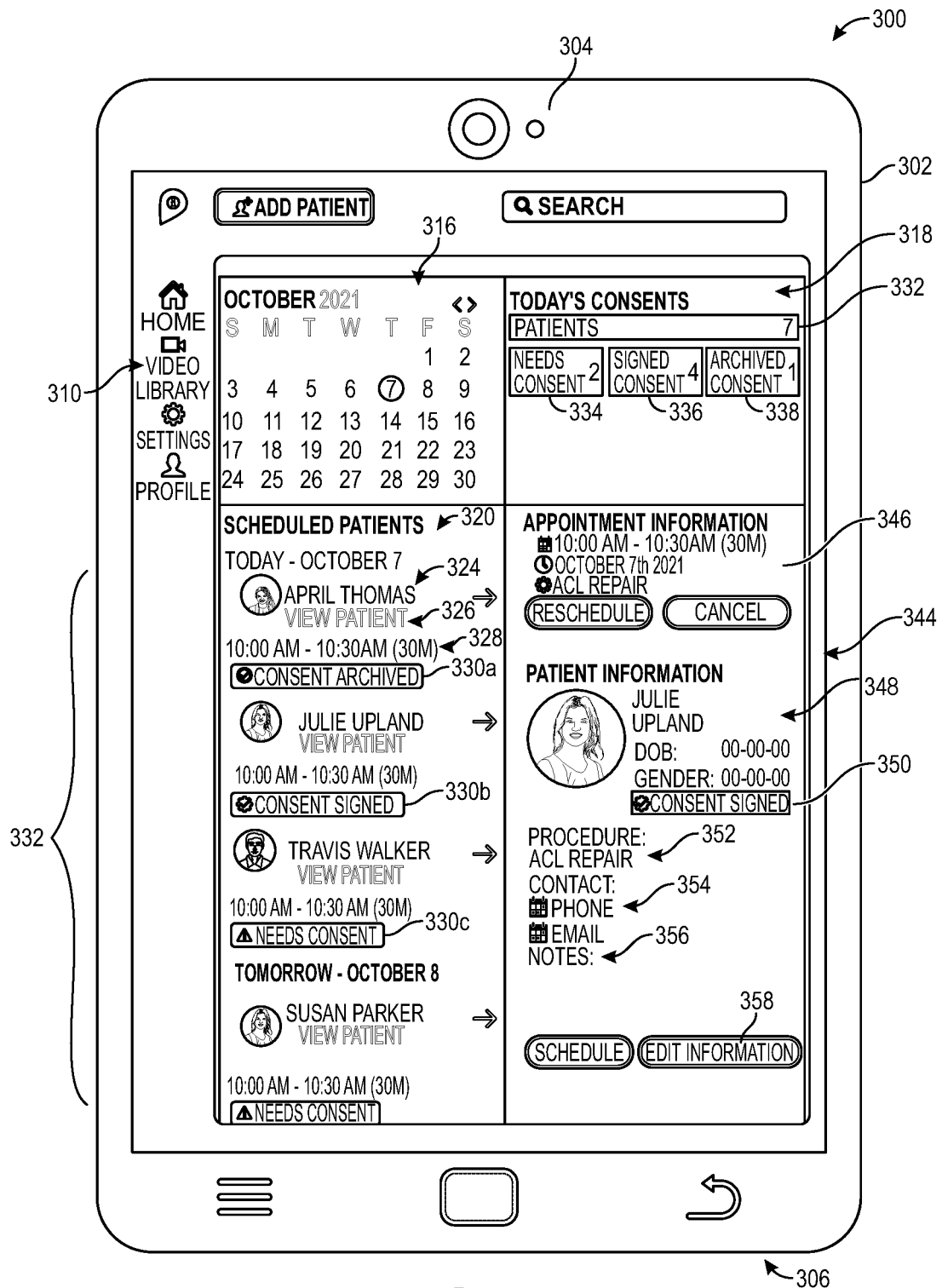
FIG. 3B illustrates a user interface of the run-time of an informed consent software in a provider mode after a patient has been selected in accordance with certain embodiments.

Turning now to FIGS. 3A-B, an exemplary embodiment of a user interface for an informed consent software in a provider mode is depicted and referred to with reference numeral 300. User interface 300 depicts a run-time of an informed consent software, which will be useful in illustrating the operation of various embodiments, as discussed in further detail below. In some embodiments, user interface 300 may be displayed on the display of a client device 302, which may be any of the client devices described above with respect to FIG. 1, including for example a tablet device. Client device 302 may comprise one or more peripherals which may be used in conjunction with an informed consent software in obtaining the informed consent of a patient. For example, client device 302 may comprise a camera 304, which may be a built-in camera of a tablet or a camera external to the tablet or client device 302. Further, client device 302 may also comprise an audio peripheral 306, which may comprise a speaker and microphone. The speaker of audio peripheral 306 may be used to provide the sound of a medical procedure video to the patient, with the microphone of audio peripheral 306 providing a means for the patient to communicate with the medical staff, log questions, input vocal commands, among other functions. It will be appreciated that client device 302 may comprise any additional peripherals, including peripherals that are yet to be discovered.

As depicted, user interface 300 includes a plurality of objects such as panes, text entry fields, buttons, clickable icons, and other interactive user interface components. In some embodiments, user interface 300 may have different features or functionalities available to a first set of users than to a second set of users. For example, the informed consent software may comprise a medical provider mode accessible by users of the informed consent software and a patient mode accessible to patients of the users. Broadly, when the informed consent software is in the provider mode, doctors, nurses, and/or other hospital or medical staff (the "users" of the informed consent software) may be provided a dashboard including a patient scheduling, patient information, calendar, prescription pads, among other features for providing medical care to patients. Because of the sensitive nature of patient data, access to doctors' schedules, writing prescriptions, and other sensitive information, the medical provider mode of the informed consent software may require certain credentials or user authority in order to access. In some embodiments, credentials may be unique to individual users, which may individualize the level of access for users when accessing the informed consent software. For example, a nurse assigned to the surgery suite of a particular hospital may be included in a surgery nurse group and may be granted access to patient records, schedules, and medication history, by way of non-limiting example. The doctors of the surgery suite of the same hospital may be included in a surgery doctor group, and may be granted access to patient records, schedules, medication history, and a feature for writing prescriptions, by way of non-limiting example.

In some embodiments, users may optionally or additionally be assigned to certain roles or assigned to groups, with the roles or groups having certain credentials and authorities to make changes to patient records, schedule procedures, or make other edits in the informed consent software. For example, groups, practices, or roles may be created by an administrator, senior engineer, or other intellectual technology professional on the backend of the informed consent software. In some embodiments, users may be sorted or assigned to at least one role, group, or practice, or may be placed in a plurality of roles, groups, or practices.

As described above, users may be sorted or organized into different roles, with each of the roles having pre-determined access to certain features or functionalities of the informed consent software, and particularly, to the provider mode as depicted by user interface 300. One such role that users may be organized into is a nurse role. In some embodiments, the nurse role may be assigned to nurses that are treating patients, which may further be assigned to a particular physician or surgeon. Through access to the informed consent software and via user interface 300, users with the nurse role may: create new patient profiles, can assign patients to a physician or surgeon, can edit the assignment, and upon a patient completing the viewing of the medical procedure video, be provided with a notice of such, for follow-up actions, among other functions.

In some embodiments, another role that users may be organized into is a physician role. In some embodiments, physicians, doctors, or surgeons may be assigned to the physician role. Through access to the informed consent software and via user interface 300, users with the physician role may: create new patient profiles, can edit the assignment, and upon a patient completing the viewing of the medical procedure video, be provided with a notice of such, for follow-up actions, among other functions In some embodiments, another role that users may be organized into is a staff role. In some embodiments, support staff such as technicians, analysts, or other support staff may be assigned to the staff role. Users assigned to the staff role may further be assigned to a particular nurse or physician, or alternatively, may be assigned to a plurality of nurses and/or physicians. Through access to the informed consent software and via user interface 300, users with the staff role may: create new patient profiles; assign patients to physicians and nurses; and edit assignments, among other functions.

In some embodiments, another role that users may be organized into is a staff supervisor role. In some embodiments, managers, shift supervisors, administrators, or other senior level employees may be assigned to a staff supervisor role and may be assigned access to certain functionalities to supervise other users. For example, through access to the informed consent software and via user interface 300, users with the staff supervisor role may: view and interact with captured analytics; create new practices and edit existing practices; assign patients to physicians and/or nurses; create new patient profiles; and assign a nurse to a physician, among other functions.

In some embodiments, another role that users may be organized into is a super administrator role. In some embodiments, high level administrators or senior software engineers, or high-level employees may be assigned to a super administrator role. For example, through access to the informed consent software and via user interface 300, users with the super administrator role may: view and interact with captured analytics, create new practices, and edit existing practices; assign roles to physicians, nurses, staff, and staff supervisors; access the web portal of the informed consent software; view patient history; and view version history of the informed consent software, among other functions.

It will be appreciated that other roles are within the scope of the embodiments, and new roles may be created depending on situations and needs that arise. It will be further appreciated that the functions, access, and features described above with respect to the roles are not intended to be limiting features, and that the roles may have functionality and accesses removed or added.

Returning to the figures, FIG. 3A depicts an exemplary run-time of an informed consent software while in a medical provider mode, which will be useful in illustrating the operation of various embodiments, as discussed in further detail below. As depicted, user interface 300 comprises a plurality of objects such as panes, text entry fields, buttons, clickable icons, or other interface components. In some embodiments, user interface 300 may comprise a visual indicator providing a visual indication that user interface 300 is in the provider mode, as opposed to in the patient mode, which is described in greater detail below. In some embodiments, the visual indicator may be a certain color of a border surrounding user interface 300. For example, while in medical provider mode, the user interface 300 may comprise a colored border (e.g., a yellow border). In some embodiments, the visual indicator may be a text box or other text-based indicator, providing a visual indication that the user interface 300 is in the medical provider mode. However, it will be appreciated that the visual indicator may be any other visual indication providing notice to a user that the user interface is in the provider mode.

As further depicted, user interface may comprise a quick info list 310, comprising various clickable icons or links, providing to a user quick access to portions of the informed consent software. For example, quick info list 310 may comprise a home icon, allowing the user to access the web portal of the informed consent software; a video library icon, allowing the user to access the medical procedure videos 210 that may be selected and played through user interface 300; a settings icon, providing the user access to the settings of the informed consent software, such as editing text size, color schemes, or changing other settings of the informed consent software; a profile icon, allowing the user to access their user profile; and an information icon, allowing a user to access a help function for searching for features of the informed consent software and/or for sending a ticket or message to an IT professional. As further depicted, user interface 300 may comprise a patient add icon 312, for adding new patients to a user's listing of patients, which is described in greater detail below. In some embodiments, upon selection of the patient add icon 312, the user may create new patient profiles 206, which may be stored in the patient record store 204. In some embodiments, user interface 300 may further comprise a search tool 314, providing for a selectable tool allowing a user to search for particular patients, physicians, or other objects in user interface 300.

Oftentimes, patient visits, medical procedures, and surgeries are scheduled days, weeks, or months in advance, and accordingly, user interface 300 may comprise a calendar pane 316, which may aid users in scheduling patients and for determining which patients are scheduled for which day. In some embodiments, calendar pane 316 may be configured as a navigable pane, allowing users to switch between and select a specific month for scheduling purposes. Further, for increased granularity, once a month has been selected, individual days of the month may be further selected.

User interface may further comprise a scheduled patient pane 320, comprising a scheduled patients listing 322. Following the selection of a particular day of a month, scheduled patient pane 320 may be generate or populated with scheduled patients listing 322, which may be a listing of the patients scheduled for appointments, procedures, or surgeries for the selected date. For example, as depicted, following selection of October $7^{th}$ through calendar pane 316, a scheduled patient listing 322 may be generated and populated in scheduled patient pane 320, providing to the user a listing of the patients scheduled for that day. In some embodiments, scheduled patient listing 322 may comprise a listing of patients for a particular physician or nurse to reduce latency and over burdening of the user.

For example, if the user accessing the informed consent software through user interface 300 is a nurse assigned to only one physician, upon selection of the date through calendar pane 316, scheduled patient listing 322 may automatically be generated and populate scheduled patient pane 320. In some embodiments, users, such as nurses, may be assigned to more than one physician and accordingly, may be assigned to more than one scheduled patient listing 322. When users are associated with more than one physician, the user may select a specific physician, and the associated scheduled patient listing 322 can populate in scheduled patient pane 320. For example, a nurse may be assigned to two physicians, with each physician having their own patient list. The nurse may select one of the two physicians, and the associated scheduled patient listing 322 may populate in scheduled patient pane 320.

Once generated, patient listing 322 may comprise one or more scheduled patient objects 324, which may be formatted to provide the name of the patient and additional information about the patient. In some embodiments, scheduled patient object 324 may comprise a selectable link 326, button, or other object, wherein responsive to selection by user, may generate a pane showing the patient profile, as described in greater detail below. Further, scheduled patient object 324 may further comprise a schedule object 328, which may be formatted as a text or graphic, providing to the user the scheduled appointment time of the selected patient. Even further, scheduled patient object 324 may further comprise a consent status object, including for example, consent status object 330a, 330b, or 330c, respectively. As depicted, the consent status object may provide a reference to the user the current status of the selected patient, and specifically whether the patient: needs to complete the informed consent process, as identified by consent status object 330a; has signed off on completing the informed consent process, but the consent has not yet been archived, as identified by consent status object 330b; has signed off on completing the informed consent process and the consent has been archived, as identified by consent status object 330c. In some embodiments, each of the consent status objects may have a unique property, such as a unique color, graphic, or design, aiding the user in identifying the consent status of the selected patient.

As further depicted, in some embodiments, user interface 300 may comprise a consents pane 318, providing a reference to the user about the number of consents and the status of consents for a selected date. For example, consents pane 318 may comprise a patients object 332, a needs consent object 334, a signed consent object 336, and an archived consent object 338. In some embodiments, patients object 332 may comprise a graphic or text displaying the number of patients scheduled for the selected date. Accordingly, consents object 318 may be linked or otherwise connected to patients listing 322, providing a reference to the total number of patients scheduled for the selected date rather than information about an individual patient. Further, needs consent object 334, signed consent object 336, and archived consent object 338 may likewise be linked or otherwise connected to the patients listing 322 and more particularly to the consent status objects included in the scheduled patients listings. Like patients object 332, each of the needs consent object 334, signed consent object 336, and archived consent object 338 may provide a reference to the user about the current status of all the patients of a selected date, rather than the specific status of individual patients. Accordingly, user interface 300 may provide information to the user at a relatively micro level, as provided by scheduled patient pane 320 and at a relatively macro level, as provided by consents pane 318.

In some embodiments, and as depicted in FIG. 3A, user interface 300 may further comprise an all patients pane 340 comprising a listing of all patients assigned to the user. As depicted, all patients listing 342 may comprise a listing of all patients assigned to the user. All patients listing 342 may further comprise selectable icons or buttons linked to the patient profile of the selected patient. Similar to the actions selected above with the selection of a patient from scheduled patients listing, following selection, the user may edit or manipulate the client profile of the selected patient, and for example, may schedule the patient to a certain day, may assign a procedure, may assign the patient to a physician, enter notes about the patient, among other actions.

As depicted in FIG. 3B, in some embodiments, user interface 300 may provide a dynamic interface, allowing for panes and other objects to be generated and displayed or for the removal or minimization of other panes or objects. For example, responsive to a command or instruction, one or more new panes, objects, graphics, etc., may be generated and displayed in user interface 300. For example, as depicted, a user may select a patient from the scheduled patient listing 322 by activating selectable link 326. Responsive to activating the selectable link 326, patient profile pane 344 may be generated and displayed in user interface 300.

In some embodiments, patient profile pane 344 may provide information about the selected patient from data or information from the selected patient's patient profile 206. For example, the generated patient profile pane 344 may comprise an appointment information object 346. Appointment information object 346 may comprise information about the appointment scheduled for the selected patient, including the date of the appointment, the time of the appointment, and a description of the appointment. Appointment information object 346 may further comprise selectable icons or buttons, including icons to reschedule or cancel the appointment.

As further depicted in FIG. 3B, patient profile pane 344 may further comprise a patient information object 348, which may provide additional information about the selected patient. For example, personal information about the selected patient, including the patient's name, the patient's date of birth, the patient's gender, and/or additional patient information may be displayed in patient information object 348. In some embodiments, patient information object 348 may further comprise a consent status object 350, which may be configured in the same manner as consent status objects as described above with respect to 330a, 330b, and 330c, providing a reference to the consent status of the selected patient.

As further depicted in FIG. 3B, patient profile pane 344 may comprise additional objects for providing patient information, including for example: a procedure object 352, for providing a description of the procedure the patient is scheduled for; a contact object 354, for providing contact information about the patient, which may be useful for follow-ups or for contacting the patient; and/or a notes object 356, providing the user an entry field for entering notes about the patient, such as the patient's current status, questions asked by the patient, concerns expressed by the patient, or other notes that may be made during a patient consultation or visit. Patient profile pane 344 may further comprise an edit information icon 358, providing a selectable icon allowing the user to add, delete, or otherwise edit the information provided in the patient profile pane 344. In some embodiments, patient profile pane 344 may comprise two edit information icons 358, with one icon selectable for confirming the scheduling of the patient and one icon selectable to edit the patient's information.

Figure 3C:
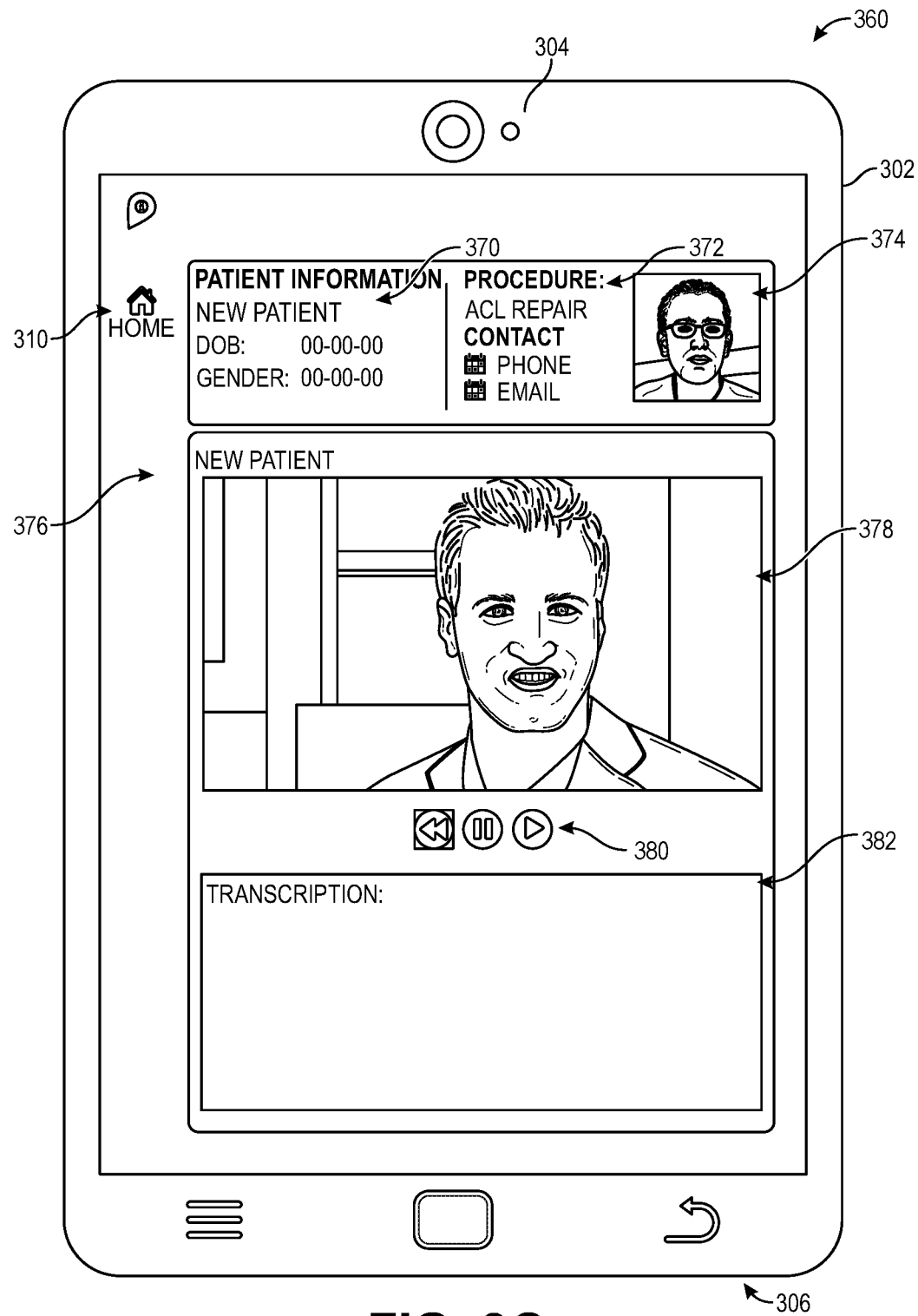
FIG. 3C illustrates a user interface of the run-time of an informed consent software in a patient mode in accordance with certain embodiments.
Figure 3D:
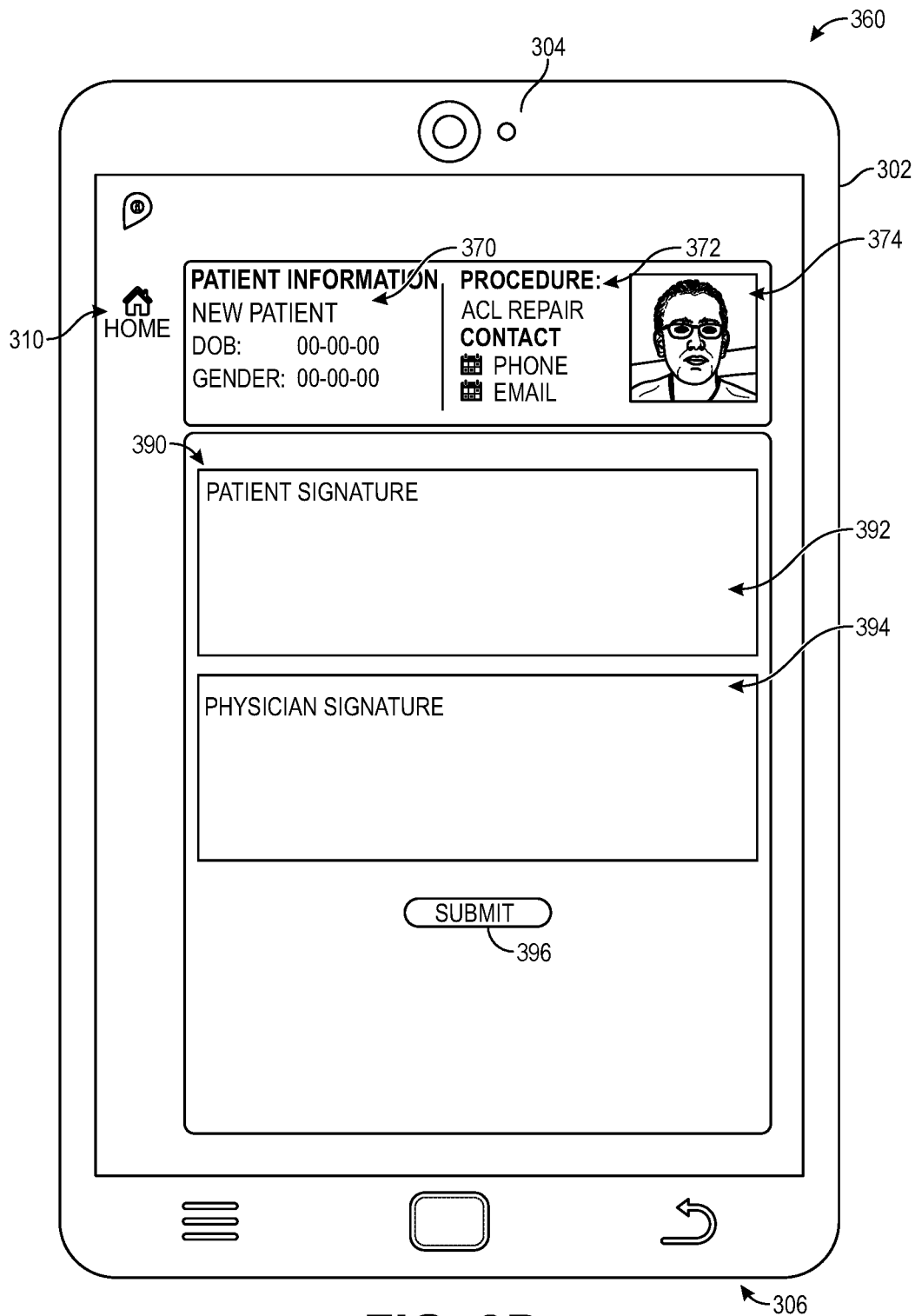
FIG. 3D illustrates a user interface of the run-time of an informed consent software in a patient mode for obtaining an affirmative consent in accordance with certain embodiments.

Turning now to FIGS. 3C-3D, an exemplary embodiment of a user interface for the informed consent software in a patient mode is depicted and referred to with reference numeral 360. In some embodiments, user interface 360 may comprise a visual indicator providing a visual indication that user interface 360 is in the patient mode, as opposed to in the medical provider mode. In some embodiments, the visual indicator may be a certain color of a border surrounding user interface 360. For example, while in patient mode, the user interface 360 may comprise a green border. In some embodiments, the visual indicator may be a text box or other text-based indicator, providing a visual indication that the user interface 360 is in the patient mode. However, it will be appreciated that the visual indicator may be any other visual indication providing notice to a user or patient that the user interface is in the patient mode.

In some embodiments, following the selection of a patient from scheduled patient listing 322, user interface 300 may transition from the provider mode to the user interface 360 of the patient mode. In some embodiments, prior to the transition from provider mode to patient mode, the patient may confirm that they are the correct patient and/or that the correct procedure has been selected. For example, in some embodiments, the patient may be required to log in to the informed consent software through a username and password. In some embodiments, the user interface may not transition from the provider mode to the patient mode until the patient has been authenticated.

In some embodiments, the user and the patient may be in the same location and the client device 302 may be physically given to the patient. In some embodiments, the patient may access user interface 360 from a second client device running the informed consent software, rather than from the client device 302 used by the user. For example, as telemedicine continues to expand, medical providers may perform the steps described above in a separate location from the patient. Accordingly, a patient may access the informed consent software via user interface 360 from their home or other location. Similar to the provider mode as described above with respect to FIGS. 3A-3B, user interface 360 may comprise a plurality of objects, such as panes, text entry fields, buttons, messages, or other user interface components. Embodiments of the invention include the patient viewing a video on the client device at a remote location, e.g., at the patient's home.

When in the patient mode, user interface 360 may be presented to the patient in a similar manner as described above with respect to the user interface 300 of the medical provider mode. For example, user interface 360 may be displayed on the display of client device 302 and may comprise some of the same objects, or stripped-down objects that are present in the medical provider mode. While in patient mode, it may be necessary to limit features, functionality, or access capabilities of the user interface, to prevent patients from accessing patient histories or records of other patients or other sensitive hospital information. Accordingly, in some embodiments, while in patient mode, the user interface 360 may comprise a paired down quick info list 310, and for example, may comprise the home icon and the information icon. However, it will be appreciated that in some embodiments, the patient mode of user interface 360 may comprise more selectable icons in the quick info list 310, including for example, selectable icons that are not present in the medical provider mode. By way of non-limiting example, an additional icon that may be present in the patient mode of user interface 360 may be a messaging icon, providing a messaging means for the patient to contact a medical professional if the patient has any questions or concerns regarding the medical procedure video 210.

In some embodiments, user interface 360 may comprise a patient information pane 370, comprising information about the patient. Information included in the patient information pane 370 may include, but are not limited to, the patient's name, the patient's date of birth, the patient's gender, physical characteristics about the patient, the patient's profile 206 account number or identifier, among other information. As described below, the patient may review the information in patient information pane 370 and verify the information.

As depicted, user interface 360 may comprise an additional information pane 372, comprising additional information that may be useful to the patient when watching the medical procedure video 210. For example, additional information pane 372 may comprise a description of the procedure, informing the patient of exactly which procedure the patient will undergo, such as an ACL repair or gastric by-pass. This may act as a further quality assurance test, as if the description of the procedure does not match what the patient is scheduled for, the patient may alert a medical professional.

As further depicted in FIG. 3C, user interface 360 may comprise a patient display window 374, which as described in greater detail below, may be used to establish a record that a patient has watched the medical procedure video 210, and has been informed of what the medical procedure entails, including any risks or potential complications associated with the procedure. In some embodiments, when the patient is viewing and watching the medical procedure video 210, camera 304 of client device 302 may be used to capture an image of the patient watching the medical procedure video 210 and display the captured image on patient display window 374 in real time. As described in greater detail below, through displaying a real-time image of the patient watching the medical procedure video 210, a permanent record is in place providing evidence that the patient has watched the medical procedure video 210.

As further depicted in FIG. 3C, user interface 300 may comprise a medical procedure video pane 376, providing a display for playing the medical procedure video 210 to the patient. In some embodiments, medical procedure video pane 376 may comprise a medical procedure video window 378, video controls 380, an/or a transcription pane 382. Upon verification of the correct patient and after selection of the correct medical procedure video 210, the medical procedure video 210 may be displayed in medical procedure video window 378. In some embodiments, medical procedure video pane 376 may further comprise video controls 380, For example, video controls 380 may be selectable icons, buttons, or other controls for controlling certain aspects of the medical procedure video 210. For example, video controls 380 may comprise selectable icons allowing the patient to play, pause, or re-wind the medical procedure video 210. Video controls 380 may comprise additional selectable icons, allowing the patient additional options while viewing the medical procedure video. For example, video controls 380 may further comprise a bookmarking feature, allowing the patient to bookmark a particular section of the medical procedure video 210. Video controls 380 may also comprise a messaging feature, allowing the patient to send a message to a medical professional. Video controls 380 may also comprise a related videos feature, allowing patients to select and load videos that are related to the medical procedure video 210 they are watching. For example, if the patient is scheduled for an ACL repair, upon completion of watching the medical procedure video 210 associated with an ACL repair, the user may select another video describing the rehab process of an ACL repair. Video controls 380 may also comprise any additional features that may aid the patient in viewing and comprehending the medical procedure video. For example, video controls 380 may comprise a voice activated feature, responsive to verbal commands from a patient or other user.

As depicted, in some embodiments, the panes and/or windows of user interface 300 and/or user interface 360 may be separated from other panes and/or windows, providing partitions to avoid overlapping. However, in some embodiments, panes and/or windows including patient display window 374 and medical procedure video window 378 may at least partially overlap another pane and/or window. Further, in some embodiments, two or more panes and/or windows may be combined, providing for a single pane and/or window. For example, in some embodiments, patient display window 373 and medical procedure video window 378 may be combined into a single window, with each of the captured image of the patient and the medical procedure video 210 displayed in a single window.

In some embodiments, user interface 360 may further comprise a transcription pane 382, which may be configured for presenting a text-based transcript description of the medical procedure video 210. Through such text-based transcript, patients that are audio impaired may read the transcript while medical procedure video 210 plays in medical procedure video window 378. Additionally, a text-based transcript may also be helpful to patients without an audio impairment, providing a text-based reference that a patient may refer to as opposed to re-winding the medical procedure video 210. In some embodiments, the medical procedure video 210 may be accompanied with a file comprising a transcript of the video, and while the medical procedure video 210 is playing in medical procedure video window 378, the transcript may populate in transcription pane 382.

In addition to presenting the medical procedure video 210, the informed consent software may additionally be configured to record the process, providing a saved record that the patient has viewed the medical procedure video 210 and consents to the procedure as described. Through a recording program, application, or other software, the informed consent software may be configured for recording a video of at least a portion of the display of client device 302. In some embodiments, the recording of the display may be an automatic process, without requiring a command from a user or patient to begin recording of the display. For example, upon transition from medical provider mode to patient mode, the informed consent software may begin recording the display of client device 302. In some embodiments, when the patient begins playing the medical procedure video 210, the informed consent software may begin recording the display of client device. In some embodiments, the recording of the display of client device may be a manual process, requiring a command or prompt by the patient or anther user to begin recording. For example, in some embodiments a selectable record icon may be present in user interface 360. In some embodiments, recording of the display may be prompted through a voice command. The informed consent software may further comprise a past footage recording feature, which may be configured for recording a set period after the recording process begins. For example, responsive to selecting a record icon, the informed consent software may begin recording the display of client device 302 as well as capturing the previous five minutes of display. It will be appreciated that the length of time of the past footage recording may be customizable and that any length of time of past footage recording may be selected.

In some embodiments, the informed consent software may be configured to capture and record the entire display of client device 302 and save the captured recording as a single video file. For example, the captured recording may comprise the entirety of user interface 360, including patient display window 374 and medical procedure video pane 376. Through recording the entirety of the display of client device 302, the need to sync multiple video tracks at a later time is eliminated. Further, through recording the entirety of the display of client device 302, the fidelity of the authenticity of the captured image in relation to the medical procedure video 210 can be ensured.

In some embodiments, individual portions of the display of client device 302 may optionally and/or additionally be recorded as separate files, which may be synched and/or combined at a later time. For example, patient display window 374, or the raw footage of the patient, may be separately recorded from medical procedure video window 478, providing for a separate video file of the patient as the patient is watching the medical procedure video 210. The separately recorded video of the patient may then be saved and archived. The separately recorded video of the patient may then be synced and combined with medical procedure video 210, providing a record that the patient did in fact watch the medical procedure video 210. In some embodiments, recording and saving the video of the patient as a separate video file may aid in providing a backup or safeguard in the event that the captured recording of the entire display of client device 302 becomes corrupted or becomes unusable. In some embodiments, medical procedure video 210 may also be saved as a separate video file. In some embodiments, a live or in-person description or event may be used in place of medical procedure video 210, and the raw footage of the live or in-person description may be recorded and saved as a separate video file.

Further, additional and/or optional techniques may be used to aid in determining whether a tampering of the video recording of the user interface 360 has occurred. For example, a non-limiting example of such techniques may include synching: (1) the audio and the video of the medical procedure video 210, (2) the raw or native video of the patient captured by camera 304 and displayed in patient display window 374, and (3) the recorded video of the user interface 360 during the playing of the medical procedure video 210. Further, the informed consent software may additionally and/or optionally comprise synching tools or techniques, which may aid in synching multiple video fields and/or multiple audio files. For example, prior to playing the medical procedure video 210, the patient may be required to provide verbal responses to prompts generated by the informed consent software, to aid in synching the multiple videos and/or audio files.

In some embodiments, the medical procedure video window 378 may be configured for displaying a live or in-person description of a medical procedure instead of displaying the medical procedure video 210. In certain scenarios or circumstances, it may not be possible for a medical procedure video 210 to be displayed in medical procedure video window 378. For example, new or novel procedures may not have a dedicated medical procedure video 210 made or created for describing the procedure, and a physician, nurse, or other medical professional may be required to give a description of the procedure to the patient in person. By way of another non-limiting example, a live or in-person description may be required in the event of a disconnection event between hospital server 202 and medical procedure video server 208 or between hospital server 202 and client device 302, wherein a medical procedure video 210 cannot be displayed on client device. The informed consent software may still be configured to capture and record the medical professional giving the description. For example, the client device 302 may comprise an additional camera, such as a rear-facing camera, or a separate camera peripheral in communication with client device 302, which may be used to capture a recording of the medical professional providing the description of the procedure to the patient. Similar to how camera 304 may capture an image of the patient and display the patient display window 374, the captured image of the medical professional may be displayed in the medical procedure video window 378, and the process of providing the description of the medical procedure and obtaining consent from the patient may proceed in the manner described herein.

In some embodiments, the recording of the display of client device 302 may act as a passive informed consent of the patient. For example, the passive informed consent may be evidence of the patient consenting to the medical procedure, without an affirmative act by the patient, in which the affirmative act may be a signature, verbal acknowledgment, or other affirmative action by the patient acknowledging that the patient consents to the procedure. The passive informed consent of the patient may be used in combination with, or in place of an affirmative consent of the patient, as described below. For example, the medical procedure video 210 may outline the details of an upcoming medical procedure, including any associated risks or potential complications. If the patient completes viewing the medical procedure video 210 without raising any objections to the procedure, the recording of the patient may serve as evidence that the patient has been presented with a description of the medical procedure, including any risks or potential complications. This can prevent the patient from later claiming that they were not warned of risks or complications associated with the procedure.

Following completion of the medical procedure video 210, the informed consent software may also be configured for obtaining an affirmative consent from the patient, acting as an acknowledgment that the patient has viewed and understood the medical procedure video. For example, an exemplary embodiment of user interface 300 configured for obtaining an informed consent of a patient is depicted in FIG. 3D. For example, in some embodiments, user interface 300 may comprise a consent pane 390. In some embodiments, following the completion of the medical procedure video 210, consent pane 390 may be generated and displayed in user interface 300. As depicted, in some embodiments, consent pane 390 may replace medical procedure video window 378 within user interface 300.

In some embodiments, consent pane 390 may be superimposed over medical procedure video window 378. Consent pane 390 may comprise a patient consent signature pane 392. Patient consent signature pane 392 may comprise a selectable and editable text box, providing an interface for the patient to enter a signature, initials, or other acknowledgement (e.g., a verbal acknowledgment) that the patient has viewed the medical procedure video 210. Additionally, in some embodiments, consent pane 390 may comprise a provider signature pane 394. Like patient consent signature pane 392, provider signature pane 394 may comprise a selectable and editable text box, providing an interface for the medical provider to enter a signature, initials, or other acknowledgement that the patient has viewed the medical procedure video 210 and/or has signed patient consent signature pane.

As depicted, consent pane 390 may further comprise a selectable submission icon 396 allowing the patient and/or medical provider to submit the signatures entered via patient consent signature pane 392 and/or provider signature pane 394 for storage and archiving. In some embodiments, upon submission, client device 302 may be returned to the medical provider and user interface 300 may transition from patient mode back to provider mode. In some embodiments, upon submission of the signatures, the patient's consent status may be updated as provided above.

In some embodiments, following the completion of the medical procedure video 210 and upon obtaining the signature of the patient and/or the medical provider, the recorded video of the display of the client device and/or the signatures may be uploaded or transmitted for storage and archiving. For example, in some embodiments, the recorded video and the signatures may be bundled together and sent to patient record store 204 for storage, including saving to the patient profile 206 of the patient. In some embodiments, the recorded video and the signatures may remain as separate files rather than bundled. In some embodiments, a copy of the recorded video and/or the signatures may be sent to the patient, providing a copy that the patient may keep in their records. In some embodiments, upon archiving of the recorded video and the signature, the patient's consent status may be updated as provided above.

The informed consent software may be further configured for tracking and/or monitoring the patient viewing the medical procedure video 210 and comprise safeguards or other methods of keeping the patient's focus on the medical procedure video 210. In some embodiments, the informed consent software may continuously monitor the position of the patient in the patient display window 374. Through such monitoring, the informed consent software can continuously monitor the positioning of the patient during the duration of the medical procedure video 210. For example, the informed consent software can be configured for ensuring that the medical procedure video 210 will only play while the patient is within the field of vision of camera 304 and displayed in patient display window 374. If the patient leaves the field of vision of camera 304 and the face of the patient is no longer displayed in patient display window 374, the informed consent software may comprise a variety of techniques to cause the patient to return to the field of vison of camera 304 and accordingly, to patient display window 374.

In some embodiments, the informed consent software may be configured to automatically pause the medical procedure video 210 if the patient is no longer displayed in patient display window 374. For example, if the patient begins the medical procedure video 210 and sets the client device 302 down on a table, the informed consent software may pause the video until the patient picks up client device 302 and returns into the field of vision of camera 304. In some embodiments, the portion of patient's face and/or body necessary to be displayed in patient display window 374 may vary. For example, in some embodiments, as long as the eyes of the patient are captured by camera 304 and displayed in patient display window 374, the medical procedure video 210 may continue to play without pause. In some embodiments, the entire face of the patient may be required to be displayed in patient display window 374 to prevent medical procedure video 210 from pausing. In some embodiments, the informed consent software may be configured for tracking the eye-line of the patient and may require the patient to not only be displayed in patient display window 374 but also require the gaze of the patient to be directed to the medical procedure video window 378.

In some embodiments, the informed consent software may optionally and additionally be configured to generate a reminder or warning in the event that the patient is no longer displayed in patient display window 374. For example, if the patient begins to leave the patient display window 374, an audible chime, descriptive sound, or other warning sound may be generated and transmitted through the audio peripheral 306 of the client device 302 alerting the patient to return to viewing the medical procedure video 210. In some embodiments, if the patient begins to leave the patient display window 374, a warning may be generated and sent to an administrator of the informed consent software or the medical provider assigned to the patient, providing notice that the patient may not be watching the medical procedure video 210.

In some embodiments, in addition to monitoring the patient to ensure that the patient is watching the medical procedure video 210, the informed consent software may be further configured for facial detection to monitor the facial expressions of the patient to gauge whether the patient is understanding the material presenting in the medical procedure video 210. For example, prior to starting the medical procedure video 210, the informed consent software may conduct a baseline analysis of the patient, to gauge a natural expression of the patient. The baseline analysis of the patient may include basic questions about the patient, such as confirming the patient's name, date of birth, or other questions that the patient already knows, to establish a baseline frame of reference of the patient. As the medical procedure video 210 is playing, the informed consent software may monitor the facial expressions of the patient and compare the facial expressions against the baseline. In some embodiments, the informed consent software may utilize a machine learning algorithm for learning what facial expressions relate to certain emotions. For example, if the informed consent software determines that a patient is having difficulty understanding a portion of the medical procedure video 210, the informed consent software may pause the medical procedure video 210 and ask for confirmation that the patient is understanding the material. In some embodiments, if the informed consent software determines that a patient is having difficulty understanding a portion of the medical procedure video 210, the informed consent software may pause the medical procedure video 210 and message a nurse or other medical professional to assist the patient.

In some embodiments, the informed consent software may be configured to utilize facial recognition bio-metric techniques and technologies for authenticating users and patients. For example, in some embodiments, when a patient uses the informed consent software for a first time, the face of the patient may be captured by camera 304 and uploaded to the patient's profile 206. Accordingly, on the patient's subsequent uses of the informed consent software, the face of the patient may be captured by camera 304 and the captured image may be compared to the image uploaded to the patient's profile 206 for authenticating the patient. In some embodiments, the bio-metric authentication of the patient may be used in conjunction with traditional means of authentication, such as a username and password authentication, providing an additional layer of authenticating. In some embodiments, the bio-metric authentication of the patient may be the sole authentication means for authenticating the patient. Upon a successful authentication, the patient may be able to access user interface 360. Similar to authenticating patients, the informed consent software may likewise use bio-metric techniques and technologies for authenticating other users, such as physicians or nurses, requiring an authentication prior to granting access to user interface 300.

In some embodiments, the informed consent software may utilize metadata for analytics purposes, which may be useful for the creators of the medical procedure videos 210, by the medical providers, and/or patients for improving, modifying, and refining how the informed consent software presents information, obtains informed consent from patients, or for improving and modifying the informed consent software. In some embodiments, analytics information may be captured on a micro-level, such as for example, analytics information about individual patients. In some embodiments, the analytics information may be captured on a macro-level, such as for example, analytics information about an entire hospital, a group of hospitals, or the patients using the informed consent software. The captured analytics information may be available to administrators or other high-level users and may include, but not limited to: how many patients are accessing the informed consent software; how many medical procedure videos have been uploaded to the informed consent software; how many physicians are utilizing the informed consent software; how many nurses are utilizing the informed consent software; how many additional staff are accessing the informed consent software; how often each user is accessing the informed consent software; what days the informed consent software is being accessed, what times the informed consent software is being accessed; the length of time each user is accessing and utilizing the informed consent software; how many patients are using the informed consent software in a specified time frame; what medical procedure videos are being watched; among other analytics.

Figure 4:
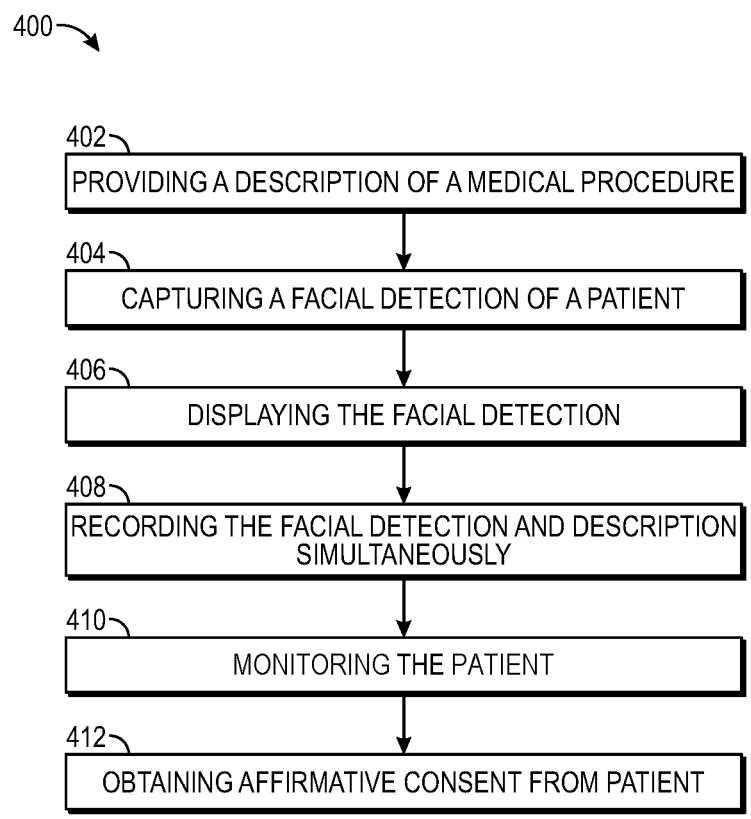
FIG. 4 illustrates an exemplary method of presenting a description of a medical procedure to a patient and obtaining the patient's informed consent in accordance with certain embodiments.

Turning now to FIG. 4, an exemplary method of obtaining an informed consent from a patient is depicted and referred to with reference numeral 400. Initially, at step 402, a description of a medical procedure may be provided to a user. In some embodiments, the description of the medical procedure may be video description, as described above with respect to medical procedure videos 210 and may be presented to the patient via a user interface of client device 302, such as a tablet. For example, a patient may be scheduled to undergo an ACL repair procedure, and the description of the medical procedure may be shown to the patient, providing an explanation of the procedure, any risks or potential complications that may arise, the benefits of the procedure, among other information.

At step 404, a facial detection of the patient viewing the medical procedure video may be captured. For example, the facial detection of the patient may be captured through a front facing camera peripheral of the client device. Accordingly, as the patient is watching the medical procedure video, the front facing camera peripheral may capture the face of the patient. For example, as the patient is watching the medical procedure video describing the ACL repair on the tablet, the front facing camera of the tablet may be directed to the patients face and record the patient as the video is playing.

At step 406, the captured facial detection of the patient may be displayed. For example, as the facial detection of the patient is captured through the front facing camera peripheral of the client device, the captured facial detection may be displayed in the user interface of the client device. In some embodiments, the captured facial detection may be simultaneously displayed as it is captured, providing a real-time display of the patient as the patient is viewing the medical procedure video. For example, as the patient is watching the medical procedure video, the image of the patient captured by the front facing camera of the tablet may be simultaneously streamed or displayed in the user interface of the tablet. In some embodiments, the user interface may comprise two display windows, with one window displaying the medical procedure video and one window displaying the captured facial detection.

At step 408, the displayed facial detection and the medical procedure video may be recorded. In some embodiments, because the facial detection and the medical procedure video are displayed simultaneously within the same user interface, both may be simultaneously recorded by recording the entirety of the user interface or display of the client device. In addition to the recording of the visuals of the user interface, the recording of step 408 may further comprise recording the audio of the medical procedure video and/or the audio of the patient. For example, as the facial detection is displayed in one window and the medical procedure video is displayed in the second window, the entirety of the user interface may be recorded at once, rather than individually recording each window separately. Through recording the entire user interface at once, issues such as synching separate video and audio tracks may be avoided, leading to greater fidelity of the authenticity of the recording. In some embodiments, recording of the user interface may occur as soon as the medical procedure video begins playing. In some embodiments, recording of the user interface may be a response to an inputted command or instruction, such as through the selection of a record icon or button. For example, the patient may be given the client device prior to the playing of the medical procedure video and may start the video procedure through controls on the client device. In some embodiments, responsive to the patient starting the medical procedure video, the client device may automatically record the user interface.

At step 410, the patient may be monitored while the patient is watching the medical procedure video. When a patient is given the client device with the medical procedure video, an attentive patient may diligently watch the medical procedure video. However, it will be appreciated that there is a risk that inattentive patients may not diligently watch the medical procedure video and may miss crucial information provided by the medical procedure video. The risk of inattentive patients may increase as telemedicine increases in use and popularity. For example, a patient may be given the client device with instructions to carefully watch the medical procedure video. However, if the patient is left alone for privacy reasons, a patient may set the client device on a table without watching the medical procedure video or may only glance at the medical procedure video. Accordingly, through tracking and/or monitoring of the patient, the manner of how the patient watches the medical procedure video may be monitored and/or recorded. For example, if the patient sets the client device down or the facial detection of the patient is no longer being captured, the medical procedure video may automatically pause. The medical procedure video may remain paused until the patient returns their gaze to the user interface and the facial detection of the patient can be captured by the camera peripheral. In some embodiments, the capturing, recording, and/or monitoring of the patient during the medical procedure video may act as a passive informed consent, providing evidence as to whether the patient did or did not watch the medical procedure video. Following completion of the medical procedure video, the recording of the user interface may be saved and sent to a storage for archiving, providing a record that the patient watched the medical procedure video.

At optional step 412, an affirmative consent of the patient may be recorded. For example, following the completion of the medical procedure video, a text box or other interactive object may be displayed in the user interface, requiring an affirmative action by the patient to enter a signature or other command recording that the patient has watched the medical procedure video and consents to the procedure including any potential risks or complications that might occur in connection with the procedure. For example, following the completion of the ACL repair video, a text box may be generated and displayed in the user interface, and request confirmation from the patient that the patient has watched the ACL repair video and consents to the procedure. Upon completion, the affirmative consent may be archived or stored, providing an additional record that the patient watched the medical procedure video.

Although the invention has been described with reference to the embodiments illustrated in the attached drawing figures, it is noted that equivalents may be employed, and substitutions made herein without departing from the scope of the invention as recited in the claims.

The invention claimed is:

1. One or more non-transitory computer-readable media storing computer-executable instructions that, when executed by a processor, perform a method for obtaining a confirmation that a viewer viewed a video, the method comprising:
providing, at a first portion of a display of a client device, the video to the viewer,
wherein the video instructs the viewer about an event that will take place after a completion of the video;
capturing, during a duration of the video, at least a portion of a face of the viewer;
displaying the portion of the face of the viewer in a second portion of the display of the client device,
wherein the first portion and the second portion are simultaneously displayed on the display of the client device;
displaying, at a third portion of the display of the client device, a text-based transcript of the video;
recording the display of the client device, wherein the first portion, the second portion, and the third portion are recorded as a captured video recording;
upon the completion of the video, obtaining the confirmation from the viewer that the viewer watched the duration of the video;
obtaining a response from the viewer to participate in the event; and
causing generation of a first selectable icon in the display of the client device,
wherein the first selectable icon is a messaging icon for the viewer to communicate with another person or with a software platform.

2. The one or more non-transitory computer-readable media of claim 1, further comprising:
causing generation of a second selectable icon in the display of the client device,
wherein the second selectable icon is a consent icon for the viewer to input the confirmation that the viewer watched the duration of the video.

3. The one or more non-transitory computer-readable media of claim 1, further comprising:
causing generation of a second selectable icon in the display of the client device,
wherein the second selectable icon is selectable by the viewer to generate a listing of related videos.

4. The one or more non-transitory computer-readable media of claim 3, further comprising:
responsive to the viewer selecting a related video from the listing of related videos, providing, at the first portion of the display of the client device, the related video to the viewer.

5. The one or more non-transitory computer-readable media of claim 1, further comprising:
causing an upload of the portion of the face of the viewer to a profile associated with the viewer; and
verifying an identity of the viewer by comparing the portion of the face of the viewer to an additional image of the viewer.

6. The one or more non-transitory computer-readable media of claim 1, further comprising:
monitoring, during the duration of the video, a facial expression of the viewer.

7. The one or more non-transitory computer-readable media of claim 1, further comprising:
tracking, during the duration of the video, a gaze of the viewer; and
pausing the video based on the gaze of the viewer.

8. A method of obtaining a confirmation that a viewer watched a video, the method comprising:
- causing generation of a first selectable icon in a display of a client device,
- wherein the first selectable icon is a messaging icon for the viewer to communicate with another person or with a software platform;
- providing, at a first portion of the display of the client device, the video to the viewer;
- capturing, during a duration of the video, an image of at least a portion of a face of the viewer,
- wherein the video is providing information, to the viewer, about an event that will take place after completion of the video;
- displaying the image in a second portion of the client device,
- wherein the first portion and the second portion are simultaneously displayed on the display of the client device;
- displaying, at a third portion of the display of the client device, a text-based transcript of the video;
- recording the display of the client device, wherein the first portion the second portion, and the third portion are recorded as a captured video recording;
- upon the completion of the video, obtaining the confirmation from the viewer that the viewer watched the duration of the video; and
- obtaining a response from the viewer to participate in the event.

9. The method of claim 8, wherein the video is a presentation given by an administrator.

10. The method of claim 8, wherein the image is captured through a camera directly coupled to the client device.

11. The method of claim 8, further comprising:
- responsive to verifying an identity of the viewer, transitioning the client device from a first mode having a first set of features and functions to a second mode having a second set of features and a second set of functions.

12. The method of claim 8, wherein the image is captured through a standalone camera separate from the client device.

13. The method of claim 8, wherein the event is a medical procedure and the video includes a description of the medical procedure, benefits of the medical procedure, and potential risks associated with the medical procedure.

14. The method of claim 8, further comprising: obtaining an additional confirmation from an administrator that the administrator provided the information about the event to the viewer.

15. One or more non-transitory computer-readable media storing computer-executable instructions that, when executed by a processor, perform a method for obtaining a confirmation that a viewer watched a video, the method comprising:
- verifying an identity of the viewer,
- wherein verifying the identity of the viewer includes a biometric authentication of the viewer;
- responsive to verifying the identity of the viewer, transitioning a client device from a first mode having a first set of features and functions to a second mode having a second set of features and functions;
- providing, at a first portion of a display of the client device, the video to the viewer,
- wherein the video instructs the viewer about an event that will take place after a completion of the video;
- capturing, during a duration of the video, an image of the viewer,
- wherein the image of the viewer is captured via a camera housed within the client device;
- displaying the image of the viewer in a second portion of the display of the client device,
- wherein the first portion and the second portion are simultaneously displayed on the display of the client device;
- recording, automatically upon transition of the client device from the first mode to the second mode, the display of the client device, wherein the first portion and the second portion are recorded as a captured video recording;
- upon the completion of the video, obtaining the confirmation from the viewer that the viewer watched the duration of the video; and
- obtaining a response from the viewer to participate in the event.

16. The one or more non-transitory computer-readable media of claim 15, further comprising:
- upon obtaining the response from the viewer, transitioning the client device from the second mode back to the first mode.

17. The one or more non-transitory computer-readable media of claim 16, wherein recording the display of the client device ends automatically upon transitioning of the client device from the second mode back to the first mode.

18. The one or more non-transitory computer-readable media of claim 17, further comprising:
- obtaining an additional confirmation from an administrator or credentialed user that the viewer watched the duration of the video.

19. The one or more non-transitory computer-readable media of claim 15, wherein the biometric authentication includes facial recognition.

20. The one or more non-transitory computer-readable media of claim 15, further comprising:
- comparing the image with an additional image of the viewer, wherein the additional image is attached to a profile associated with the viewer.

* * * * *